United States Patent
Tanaka et al.

(10) Patent No.: US 12,042,127 B2
(45) Date of Patent: Jul. 23, 2024

(54) LIGHT GUIDE UNIT AND ENDOSCOPE SYSTEM

(71) Applicant: OLYMPUS CORPORATION, Hachioji (JP)

(72) Inventors: Yoshinori Tanaka, Tokyo (JP); Satoshi Ohara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/942,465

(22) Filed: Sep. 12, 2022

(65) Prior Publication Data
US 2023/0000309 A1    Jan. 5, 2023

Related U.S. Application Data

(63) Continuation of application No. PCT/JP2020/010868, filed on Mar. 12, 2020.

(51) Int. Cl.
| | | |
|---|---|---|
| *A61B 1/005* | (2006.01) | |
| *A61B 1/00* | (2006.01) | |
| *A61B 1/06* | (2006.01) | |
| *A61B 1/07* | (2006.01) | |
| *G02B 6/42* | (2006.01) | |

(Continued)

(52) U.S. Cl.
CPC ............ *A61B 1/005* (2013.01); *A61B 1/0017* (2013.01); *A61B 1/0615* (2013.01); *A61B 1/063* (2013.01); *A61B 1/0646* (2013.01); *A61B 1/07* (2013.01); *G02B 6/42* (2013.01); *G02B 23/24* (2013.01); *G02B 23/2469* (2013.01); *G02B 23/26* (2013.01)

(58) Field of Classification Search
CPC ......... A61B 1/063; A61B 1/07; A61B 1/0615; G02B 23/2469
See application file for complete search history.

(56) References Cited

U.S. PATENT DOCUMENTS 4,569,335 A     2/1986  Tsuno
6,315,775 B1 *  11/2001 Thielen .................. A61N 5/062
                                              362/558

(Continued)

FOREIGN PATENT DOCUMENTS

JP      S59-161119 U    10/1984
JP      2004-033669 A    2/2004

(Continued)

OTHER PUBLICATIONS

Jun. 9, 2020 International Search Report issued in International Patent Application No. PCT/JP2020/010868.

(Continued)

*Primary Examiner* — William N Harris
(74) *Attorney, Agent, or Firm* — Oliff PLC

(57) ABSTRACT

A light guide unit includes a light guide member and a protection member surrounding the light guide member. The light guide member includes an optical fiber having an outer diameter. The protection member is formed in a network structure by knitting a metal member having a flat cross-sectional shape by bending the metal member in a direction in which the thickness of the metal material is thin, and a gap smaller than the outer diameter is formed along the axial direction.

20 Claims, 7 Drawing Sheets

(51) Int. Cl.
G02B 23/24 (2006.01)
G02B 23/26 (2006.01)

(56) References Cited

U.S. PATENT DOCUMENTS

| | | | |
|---|---|---|---|
| 7,433,115 B2 * | 10/2008 | Hama | A61B 1/0638 385/28 |
| 2011/0245612 A1 | 10/2011 | Nakamura | |
| 2016/0073855 A1 * | 3/2016 | Farr | A61B 1/0676 600/109 |
| 2019/0175005 A1 | 6/2019 | Tanaka | |
| 2019/0388635 A1 * | 12/2019 | Loewen | A61B 1/06 |

FOREIGN PATENT DOCUMENTS

| | | |
|---|---|---|
| JP | 2004-329539 A | 11/2004 |
| JP | 2009-077843 A | 4/2009 |
| JP | 2010-075324 A | 4/2010 |
| JP | 2011-212338 A | 10/2011 |
| JP | 2016-034353 A | 3/2016 |
| JP | 2019-051022 A | 4/2019 |
| WO | 2018/042656 A1 | 3/2018 |

OTHER PUBLICATIONS

Oct. 3, 2023 Office Action issued in Japanese Patent Application No. 2022-507123.
Feb. 27, 2024 Office Action issued in Japanese Application 2022-507123.

* cited by examiner

LIGHT GUIDE UNIT AND ENDOSCOPE SYSTEM

CROSS REFERENCE TO RELATED APPLICATIONS

This is a Continuation application of PCT Application No. PCT/JP2020/010868, filed Mar. 12, 2020, which was not published under PCT Article 21(2) in English.

TECHNICAL FIELD

The present disclosure relates to a light guide unit and an endoscope system.

BACKGROUND

The use of endoscope systems capable of early detection and early treatment of a lesion has been increasingly expanded mainly in the medical field. In addition, also in the industrial field, an endoscope system that enters the inside of a device through a slight gap and enables various inspections is widely used as a system that greatly contributes to security and safety of society.

As a light source of an endoscope system, a lamp light source such as a xenon lamp, an LED light source, and the like have been mainly used so far, but in recent years, an endoscope system using a laser light source has also started to be introduced. Laser light sources have many advantages such as high brightness, low power consumption, compactness, and fast startup, and are expected to be used more and more in the future.

When a laser is used as the light source, a video scope is required to have a structure in which high-output laser light does not leak out of a protective tube. As a situation in which light leaks from the protective tube of the video scope, basically, it is assumed that an optical fiber is damaged. Therefore, by suppressing damage of the optical fiber in the protective tube, it is possible to suppress light from leaking out of the protective tube. A technique for suppressing breakage of an optical fiber is disclosed in, for example, JP 2019-51022 A.

SUMMARY

A light guide unit according to an aspect of the present invention includes: a light guide member that guides narrow band light; a protection member that is formed of a material having heat resistance to the narrow band light and surrounds the light guide member and has flexibility due to distribution of a gap smaller than a diameter of the light guide member; and a light diffusing member that covers the protection member from outside and diffuses the narrow band light.

DESCRIPTION OF EMBODIMENTS

It is not easy to completely prevent breakage of the optical fiber. For example, even if a structure for protecting the optical fiber is thickened so that the optical fiber is not damaged by an external force, such a countermeasure is limited because a diameter of an insertion portion of the video scope is limited. In particular, in an endoscope system having a small diameter such as an oral endoscope and a nasal endoscope, it is difficult to completely prevent breakage of the optical fiber.

Figure 1:
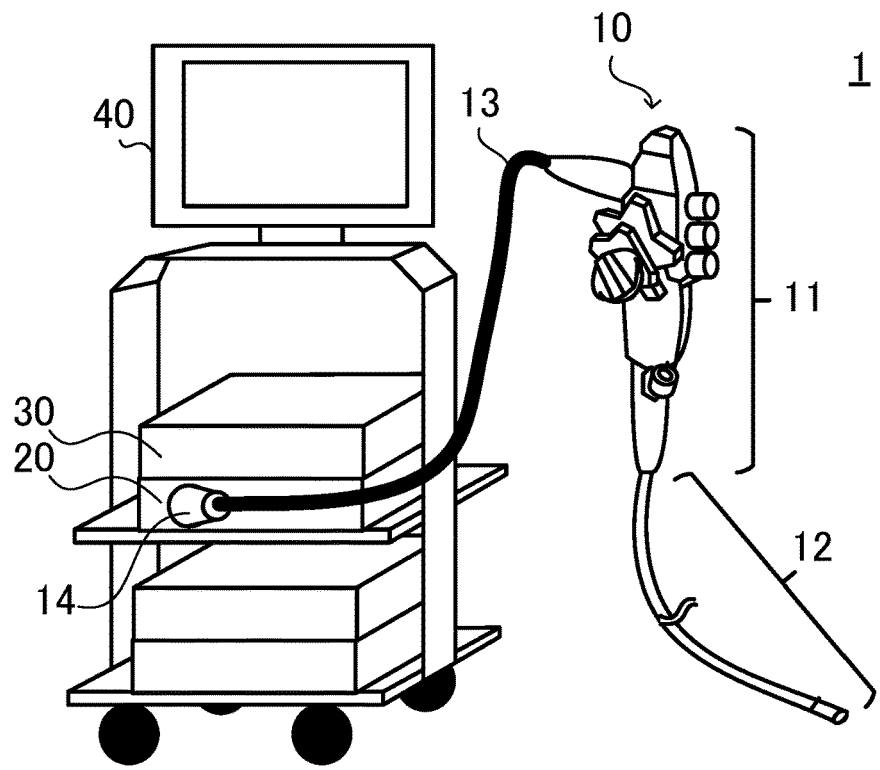
FIG. 1 is a diagram illustrating a configuration of an endoscope system.

FIG. 1 is a diagram illustrating a configuration of an endoscope system 1. Hereinafter, a configuration of the endoscope system 1 common to each embodiment will be described with reference to FIG. 1.

As illustrated in FIG. 1, the endoscope system 1 includes a video scope 10 which is an endoscope having an imaging element, and a video processor 20. The endoscope system 1 may further include a light source device 30 and a display device 40.

The video scope 10 is not particularly limited, but is, for example, a flexible endoscope. The video scope 10 may be, for example, a video scope used for examination or treatment of a respiratory system such as a bronchus, or may be a video scope used for examination or treatment of a digestive system. Furthermore, the video scope 10 is not limited to a medical video scope, and may be an industrial video scope.

As illustrated in FIG. 1, the video scope 10 includes an operation unit 11 operated by an operator, an insertion portion 12 to be inserted into a subject, a universal cord 13 extending from the operation unit 11 and connected to the video processor 20 and the light source device 30, and a connector unit 14 provided at an end of the universal cord 13. The video scope 10 outputs, to the video processor 20, an electric signal obtained by imaging the subject in a state where the insertion portion 12 is inserted into the body cavity of the subject.

The video processor 20 is a control device that controls the operation of the endoscope system 1. For example, the video processor 20 converts a signal from the video scope 10 into a video signal and displays an image of the subject on the display device 40. In addition, the video processor 20 may control the light source device 30, for example, based on the video signal, and may perform processing relating to automatic dimming control.

The light source device 30 is a device that supplies narrow band light to the video scope 10, and specifically includes a laser light source that emits laser light as narrow band light. The laser light source included in the light source device 30 is not particularly limited, but for example, emits blue laser light. In this case, the endoscope system 1 may illuminate the subject with white light in which blue and yellow light are mixed by providing a fluorescent substance that is excited by blue laser light and emits yellow light at the distal end of the video scope 10. Here, the blue laser beam has been exemplified, but the light source device 30 may emit laser beams of other wavelengths, or may switch or simultaneously emit laser beams of a plurality of different wavelengths. Specifically, the wavelength of the laser light emitted from the light source device 30 may be any wavelength in the visible light region (about 380 nm to 780 nm), for example. Furthermore, the wavelength of the laser light emitted from the light source device 30 may be outside the visible light region, and may be, for example, a wavelength in the ultraviolet region or the infrared region. Note that the light source device 30 may further include a semiconductor light source for narrow band imaging (NBI) observation, and the endoscope system 1 may appropriately switch between normal observation with white light and NBI observation.

The display device 40 is, for example, a liquid crystal display, but may be another type of display device such as an organic EL display, a plasma display, a CRT display, an LED matrix panel, electronic paper, or a projector. The endoscope system 1 may further include an endoscope hanger (not illustrated), and the video scope 10 may be hung and stored on the endoscope hanger.

Figure 2:
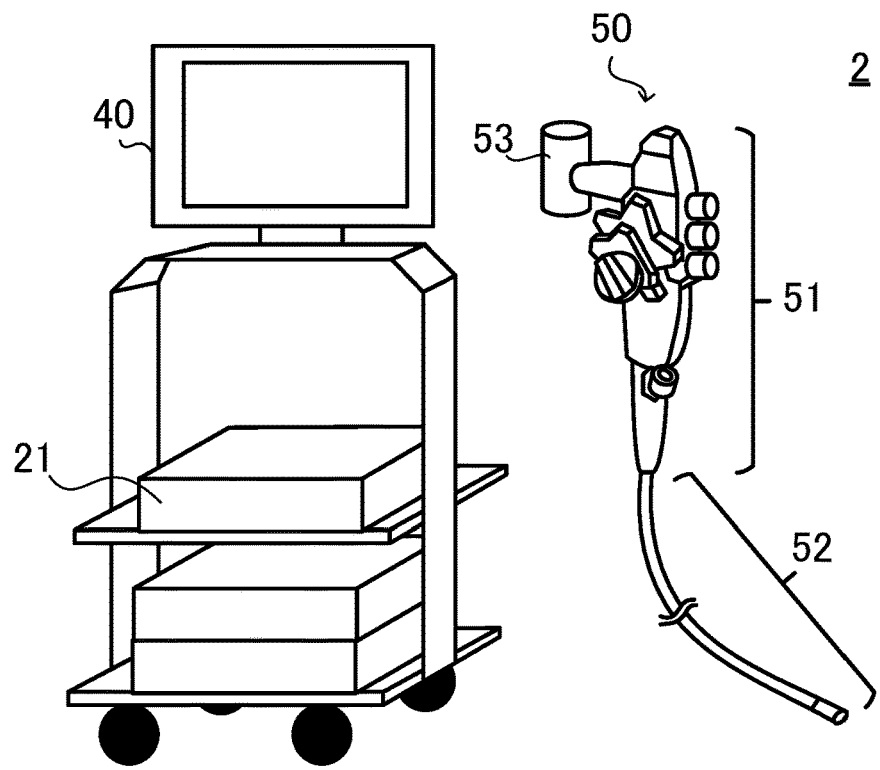
FIG. 2 is a diagram illustrating a configuration of an endoscope system.

In the endoscope system 1 illustrated in FIG. 1, the video scope 10 and the video processor 20 are connected by the universal cord 13, but the endoscope system described in the present disclosure may be, for example, a wireless endoscope system 2 in which the video scope 50 and the video processor 21 are wirelessly communicably connected as illustrated in FIG. 2. In this case, the video scope 50 included in the endoscope system 2 includes an operation unit 51 operated by the operator and an insertion portion 52 inserted into the subject, and may further include a light source device 53 instead of the light source device 30 placed on an endoscope rack. In addition, the video scope 50 may operate by power supplied from a battery provided in the video scope 50 instead of receiving power supply from a commercial power source in a wired manner.

In the endoscope system 1 configured as described above, the laser light emitted from the light source device 30 is guided by the optical fiber to the universal cord 13, the operation unit 11, and the insertion portion 12 of the video scope 10 in order, and the subject is irradiated with the laser light from the distal end of the video scope 10. That is, the insertion portion 12 of the video scope 10 is an example of a light guide unit that guides the laser light to the subject.

In the video scope 10, unlike the universal cord 13 and the operation unit 11, the insertion portion 12 is a portion to be inserted into the subject, and thus is usually designed to have a diameter as small as possible. Therefore, in the video scope 10, in general, the optical fiber is easily broken in the insertion portion 12 having a relatively thin structure surrounding the optical fiber as compared with the universal cord 13 and the operation unit 11, and if the optical fiber is broken, the laser light emitted from the optical fiber easily breaks through the relatively thin surrounding structure and leaks out.

Therefore, a light guide unit (video scope) according to each embodiment described below prevents a strong laser beam from leaking to the outside even if the optical fiber is broken by devising the structure of the insertion portion. Hereinafter, each embodiment will be specifically described.

First Embodiment

Figure 3:
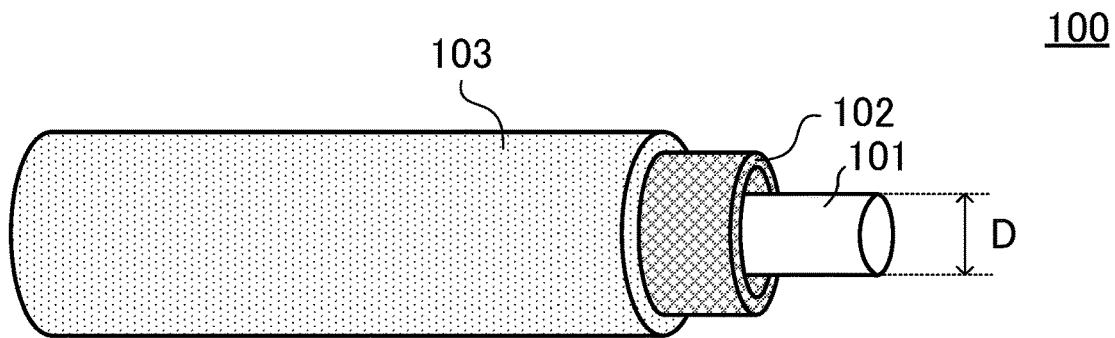
FIG. 3 is a diagram illustrating a configuration of a light guide unit according to a first embodiment.
Figure 4:
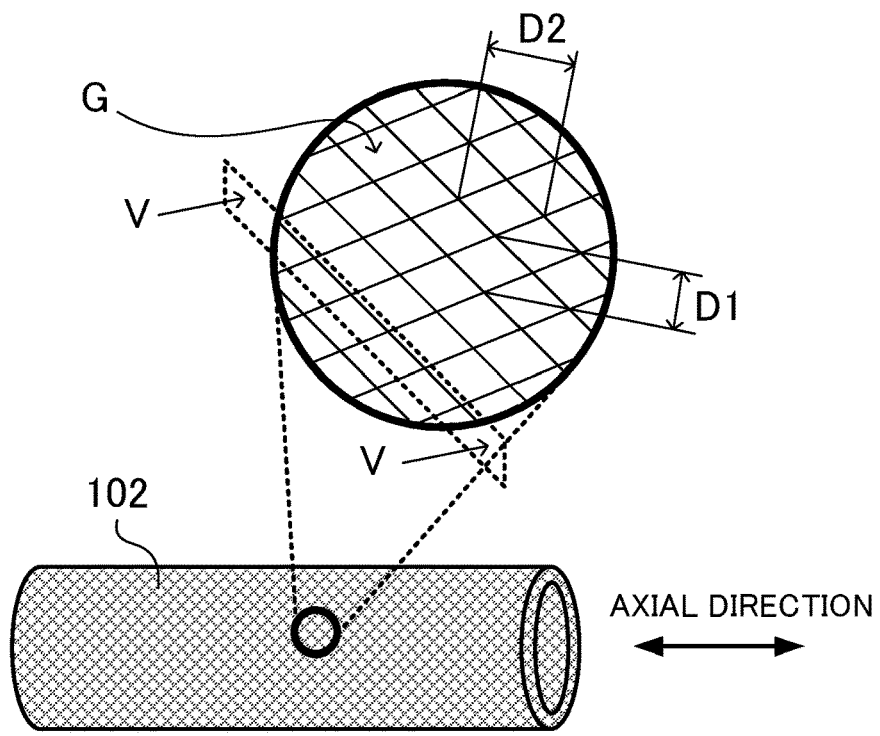
FIG. 4 is a diagram for explaining a configuration of a protection member.
Figure 5:
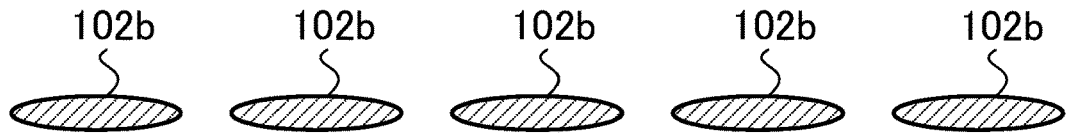
FIG. 5 is a cross-sectional view taken along line V-V in FIG. 4.
Figure 6:
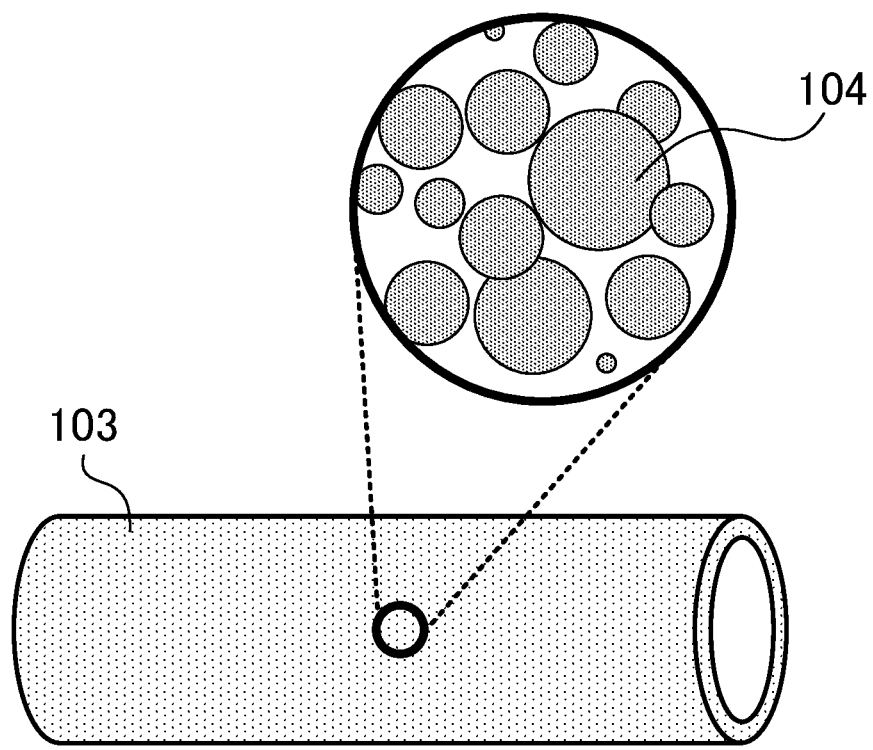
FIG. 6 is a diagram illustrating a configuration of a light diffusing member.
Figure 7:
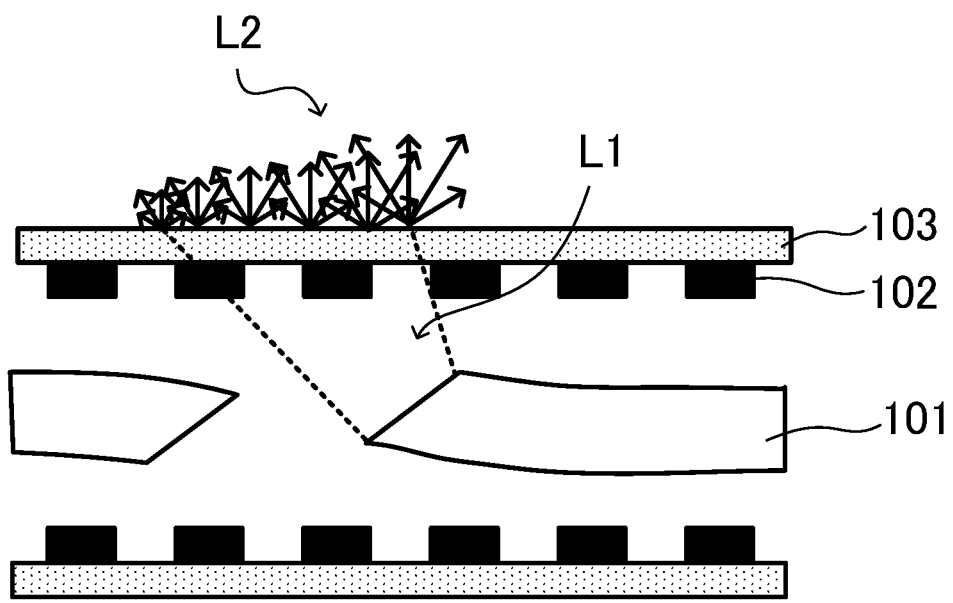
FIG. 7 is a diagram for explaining the action of the light guide unit.

FIG. 3 is a diagram illustrating a configuration of a light guide unit 100 according to the present embodiment. FIG. 4 is a diagram for explaining a configuration of a protection member 102. FIG. 5 is a cross-sectional view taken along line V-V in FIG. 4. FIG. 6 is a diagram illustrating a configuration of a light diffusing member 103. FIG. 7 is a diagram for explaining the action of the light guide unit 100. Hereinafter, a structure of an insertion portion of the light guide unit 100 will be described with reference to FIGS. 3 to 7.

As illustrated in FIG. 3, the insertion portion of the light guide unit 100 includes an optical fiber 101 that is a light guide member that guides narrow band light, a protection member 102 surrounding the optical fiber 101, and a light diffusing member 103 covering the protection member 102 from the outside. Note that the narrow band light is laser light in the present embodiment.

The optical fiber 101 is, for example, a multimode optical fiber, but the light guide member may be a bundled optical fiber in which a plurality of optical fibers are bundled. The material of the optical fiber 101 is, for example, glass, but may be another material such as plastic that is less likely to break than glass. The optical fiber 101 has a columnar shape, more desirably a cylindrical shape. Hereinafter, a case where the optical fiber 101 has an outer diameter D will be described as an example.

The protection member 102 is a member that protects a member disposed outside the protection member 102 from a member accommodated inside the protection member 102. Even if the optical fiber 101 is broken and damaged, the protection member 102 plays a role of confining the optical fiber 101 so that the broken optical fiber 101 does not break through the insertion portion and stick out to the outside. Therefore, the protection member 102 is not made of a material such as rubber that is easily melted by laser light, but is made of a material having heat resistance to at least laser light guided by the optical fiber 101. Specifically, the protection member 102 is desirably, for example, a metal material that is less likely to melt down even when irradiated with laser light.

Furthermore, the metal material used for the protection member 102 desirably has a high absorptivity with respect to the laser light guided by the optical fiber 101, and specifically desirably has a higher absorptivity with respect to white light. This is because the protection member 102 can play a role of confining the optical fiber 101 and a role of weakening the laser beam emitted from the broken optical fiber 101. More specifically, as the material of the protection member 102, stainless steel (SUS) having a high absorption rate for blue light is desirable. Note that the laser light guided by the optical fiber 101 is not limited to blue. Therefore, when the wavelength of the laser light to be guided is a color different from blue, the light guide unit desirably includes a protection member made of a material having a high absorption rate for the wavelength of the color different from blue.

In addition, the insertion portion is required to be deformed in accordance with the shape of the subject in the subject. Therefore, the protection member 102 is configured to have flexibility even when the protection member is formed of a material that is relatively hardly deformed such as metal. Specifically, the protection member 102 has flexibility due to distribution of small gaps, and desirably has a network structure formed by knitting a metal material as illustrated in FIG. 4, for example. By having the network structure made of a metal material, it is possible not only to prevent melting down even when laser light is irradiated, but also to avoid breakage of the protection member 102 even when a large force is locally applied to the protection member 102 due to contact with the optical fiber 101. Note that, in order to configure the protection member 102 to be deformable at an arbitrary position in an axial direction, it is desirable that the gaps be distributed along an axial direction of the optical fiber 101, and it is more desirable that gaps G periodically exist along the axial direction as illustrated in FIG. 4.

In addition, if the gap formed in the protection member 102 is too large, there is a possibility that the broken optical fiber 101 passes through the gap. Therefore, a gap smaller than the outer diameter of the optical fiber 101 is formed in the protection member 102. Specifically, for example, when the network structure as illustrated in FIG. 4 is formed, a diagonal length of the rectangular gap G formed by the network structure is desirably smaller than the outer diameter D of the optical fiber 101. In addition, in a case where the two diagonal lengths (a diagonal length D1 and a diagonal length D2) of the rectangle are different, the longer diagonal length D2 is desirably smaller than the outer diameter D of the optical fiber 101, and at least the shorter diagonal length D1 is desirably smaller than the outer diameter D of the optical fiber 101. Note that a cross-sectional shape of a metal material 102b constituting the protection member 102 is desirably a flat shape as illustrated in FIG. 5. This is because the metal material is a knitted, flat linear member that is bent to form a cylindrical shape. This makes it possible to include small gaps in the metal material and maintain high flexibility as compared with a case of knitting the metal material having a cylindrical cross-sectional shape.

The light diffusing member 103 is a member that diffuses the light incident on the light diffusing member 103 inside or on a surface of the light diffusing member 103 and emits the diffused light from the light diffusing member 103. Even if the optical fiber 101 is broken and damaged, the light diffusing member 103 plays a role of reliably and sufficiently weakening the light intensity per unit area of the laser light emitted from the broken optical fiber 101. In order to achieve the purpose of reliably and sufficiently weakening the light intensity, a light diffusing member that diffuses the laser light is used for the light diffusing member 103 instead of a light shielding member that shields the laser light by absorbing the laser light. This is because a light diffusing member that diffuses light is less likely to be destroyed by laser light than a light shielding member that absorbs light.

Specifically, for example, as illustrated in FIG. 6, the light diffusing member 103 may contain fine particles such as silica as light diffusion particles 104, and the laser light may be diffused by the light diffusion particles 104. The light diffusion particles are not particularly limited. Any light diffusion particle can be adopted for the light diffusing member 103. As a result, as illustrated in FIG. 7, laser light L1 emitted from the broken optical fiber 101 is diffused by the light diffusion particles 104, and diffused light L2 having a weakened light intensity per unit area is emitted from the light diffusing member 103, so that it is possible to prevent the strong laser light from leaking from the insertion portion.

According to the light guide unit 100 configured as described above, even if the optical fiber 101 is damaged, it is possible to prevent strong light from leaking from the light guide unit 100 to the outside. Therefore, even when restriction is imposed on the diameter of the insertion portion as in the endoscope system 1, the laser light source can be adopted as the light source of the endoscope system.

Figure 8:
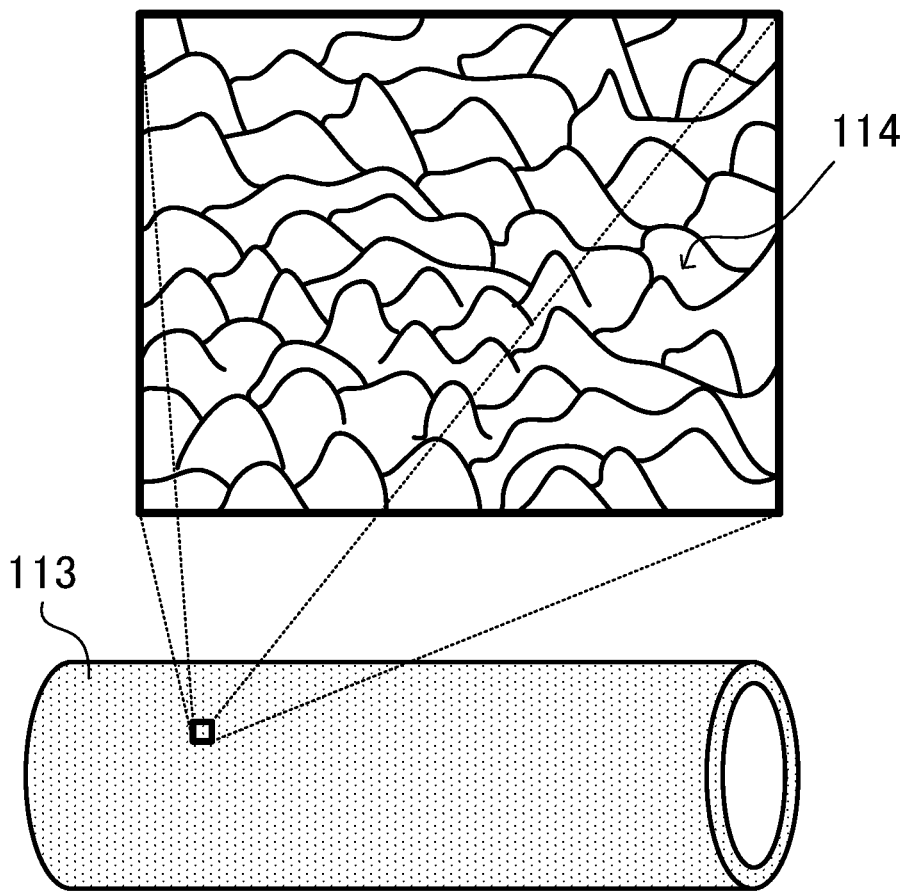
FIG. 8 is a diagram illustrating a configuration of the light diffusing member.

FIG. 8 is a diagram illustrating a configuration of a light diffusing member 113. The light guide unit 100 may include the light diffusing member 113 illustrated in FIG. 8 instead of the light diffusing member 103 containing the light diffusion particles. The light diffusing member 113 is a light diffusing member that diffuses laser light with irregular bumps 114 formed on the surface. Even in a case where the light diffusing member 113 is provided instead of the light diffusing member 103, it is possible to prevent strong laser light from leaking out of the insertion portion, similarly to a case where the light diffusing member 103 is provided.

As described above, the structure in which the light diffusing member diffuses light may be the light diffusion particles contained in the light diffusing member or the bumps formed on the surface of the light diffusing member, and in any case, the light diffusing member is configured to be translucent in order to transmit light. This feature makes it possible to have a manufacturing advantage in that it is possible to cure the adhesive applied to the inner side of the light diffusing member with the ultraviolet ray irradiated from the outside in the manufacturing process of the light guide unit.

Second Embodiment

Figure 9:
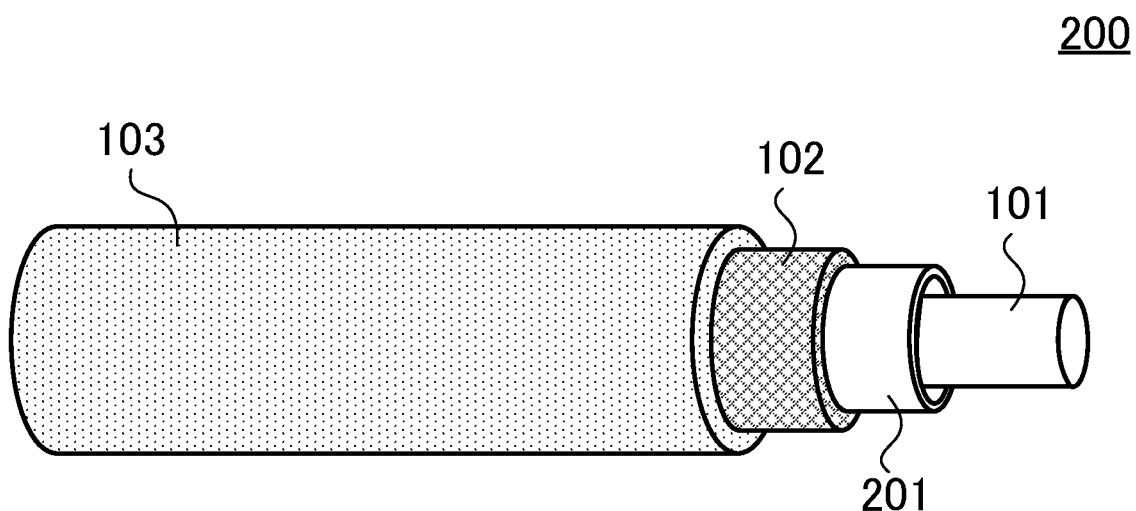
FIG. 9 is a diagram illustrating a configuration of a light guide unit according to a second embodiment.
Figure 10:
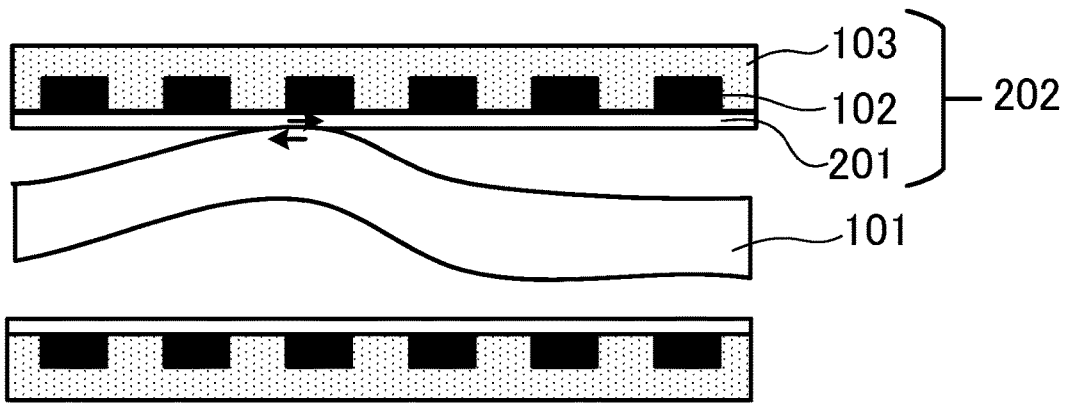
FIG. 10 is a diagram for explaining the action of the light guide unit.

FIG. 9 is a diagram illustrating a configuration of a light guide unit 200 according to the present embodiment. FIG. 10 is a diagram for explaining the action of the light guide unit 200. Hereinafter, a structure of an insertion portion of the light guide unit 200 will be described with reference to FIGS. 9 and 10.

As illustrated in FIGS. 9 and 10, the light guide unit 200 is different from the light guide unit 100 in including a friction reducing member 201 that covers the protection member 102 from the inside. Note that the optical fiber 101 is accommodated inside the friction reducing member 201. The other points are similar to those of the light guide unit 100.

The friction reducing member 201 is a member provided between the members for the purpose of reducing a frictional force, and specifically, is a member that generates a frictional force smaller than a frictional force generated between the members when the friction reducing member 201 is not provided between the friction reducing member 201 and each member. The friction reducing member 201 plays a role of avoiding generation of a large frictional force when the side surface of the optical fiber 101 comes into contact with the protection member 102 during normal use of the light guide unit 200, and instead, and preventing the optical fiber 101 from being damaged by friction with the protection member 102 by the side surface of the optical fiber 101 coming into contact with the friction reducing member 201 having a lower friction coefficient than the protection member 102. As described above in the first embodiment, the protection member 102 has, for example, a network structure made of a metal material. Therefore, when the optical fiber 101 is in direct contact with the protection member 102, a large friction occurs between the optical fiber 101 and the protection member 102, and the surface (side surface) of the optical fiber 101 made of glass or plastic is damaged. The friction reducing member 201 covers the protection member 102 from the inside to prevent such a large friction from occurring. A material having a low friction coefficient is desirably used for the friction reducing member 201, and for example, but not limited to, a fluororesin such as poly tetrafluoroethylene (PTFE) may be used.

As illustrated in FIG. 10, it is desirable that the friction reducing member 201, the protection member 102, and the light diffusing member 103 are integrally formed without a gap. Hereinafter, these are collectively referred to as a braided tube 202. A specific method of manufacturing the braided tube 202 is not particularly limited, but for example, the braided tube 202 may be formed by winding a metal material on the friction reducing member 201 to form the protection member 102 having a network structure, and further press bonding the light diffusing member 103 thereon.

According to the light guide unit 200 configured as described above, also, similarly to the light guide unit 100, even if the optical fiber 101 is damaged, it is possible to prevent strong light from leaking from the light guide unit 200 to the outside. In addition, according to the light guide unit 200, it is possible to prevent the optical fiber 101 from being damaged during normal use, and thus, it is possible to maintain the performance of the light guide unit 200 for a long period of time. In addition, since it is possible to prevent the optical fiber 101 from being damaged in the process of inserting the optical fiber 101 into the braided tube 202 at the time of manufacturing, it is also possible to expect improvement in yield and reduction in an initial defect rate.

Third Embodiment

Figure 11:
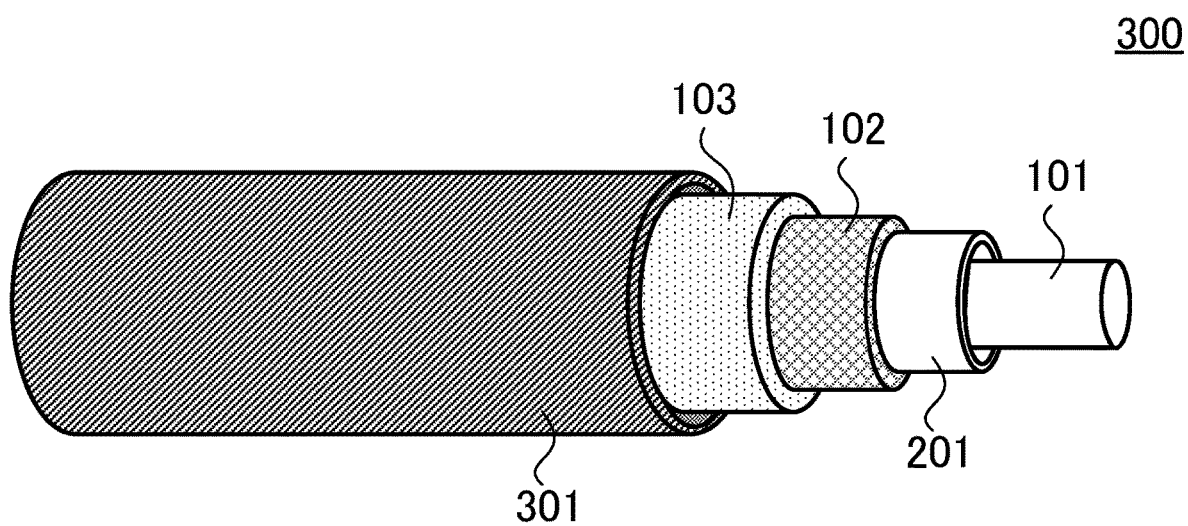
FIG. 11 is a diagram illustrating a configuration of a light guide unit according to a third embodiment.
Figure 12:
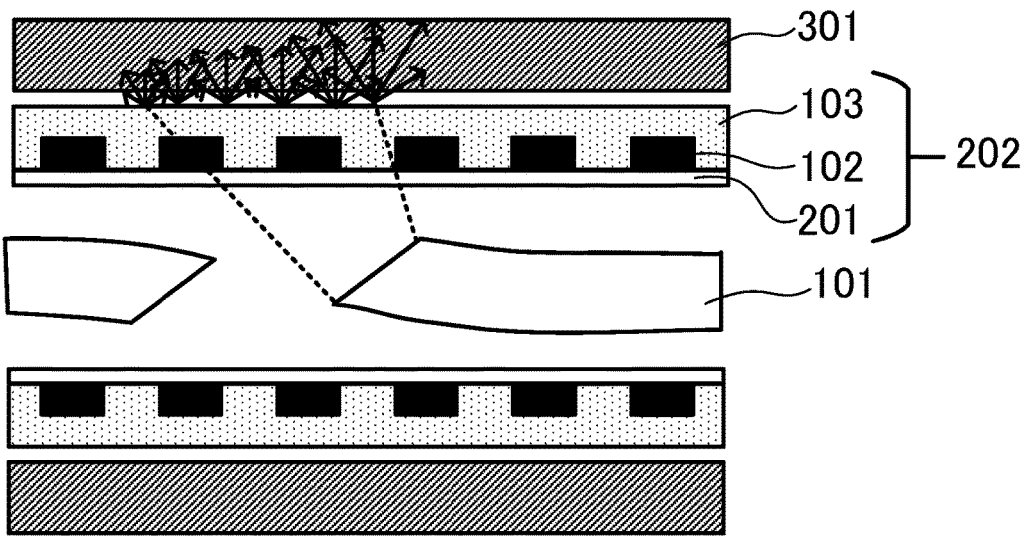
FIG. 12 is a diagram for explaining the action of the light guide unit.

FIG. 11 is a diagram illustrating a configuration of a light guide unit 300 according to the present embodiment. FIG. 12 is a diagram for explaining the action of the light guide unit 300. Hereinafter, a structure of an insertion portion of the light guide unit 300 will be described with reference to FIGS. 11 and 12.

As illustrated in FIGS. 11 and 12, the light guide unit 300 is different from the light guide unit 200 in that the light guide unit 300 includes a light shielding member 301 that surrounds the light diffusing member 103 and shields the light diffused by the light diffusing member 103. The other points are similar to those of the light guide unit 200.

The light shielding member 301 is a member that prevents light from passing through the light shielding member 301 by absorbing light incident on the light shielding member 301. The light shielding member 301 plays a role of preventing the laser light from leaking to the outside of the insertion portion by absorbing the laser light with weakened light intensity diffused by the light diffusing member 103. The light shielding member 301 has, for example, a cylindrical shape made of an elastic member such as rubber, and accommodates the optical fiber 101 and the braided tube 202 in a hollow portion thereof. A thickness of the light shielding member 301 may be adjusted to a thickness within a range in which the insertion portion falls within an allowable diameter and to an extent that laser light can be shielded.

According to the light guide unit 300 configured as described above, even if the optical fiber 101 is damaged, it is possible to prevent light from leaking from the light guide unit 300 to the outside. In addition, it is similar to the light guide unit 200 in that damage of the optical fiber 101 during normal use and manufacturing can be prevented.

Fourth Embodiment

Figure 13:
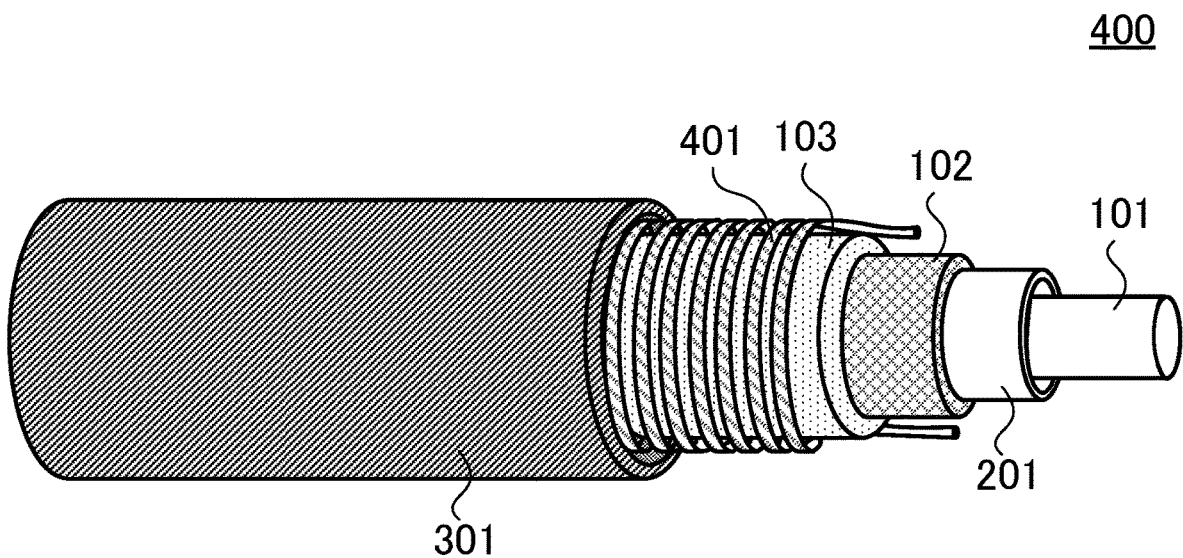
FIG. 13 is a diagram illustrating a configuration of a light guide unit according to a fourth embodiment.
Figure 14:
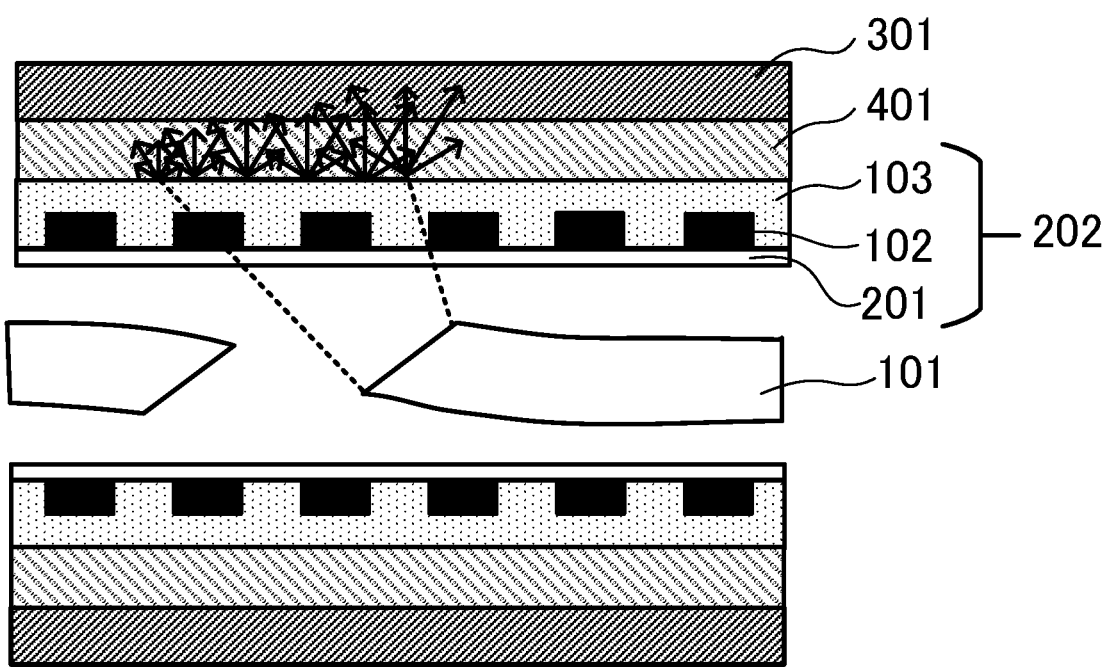
FIG. 14 is a diagram for explaining the action of the light guide unit.

FIG. 13 is a diagram illustrating a configuration of a light guide unit 400 according to the present embodiment. FIG. 14 is a diagram for explaining the action of the light guide unit 400. Hereinafter, a structure of an insertion portion of the light guide unit 400 will be described with reference to FIGS. 13 and 14.

As illustrated in FIGS. 13 and 14, the light guide unit 400 is different from the light guide unit 300 in including a spacing member 401 that holds an interval between the light diffusing member 103 and the light shielding member 301 within a predetermined range. The other points are similar to those of the light guide unit 300.

The spacing member 401 is a member that is provided between members to keep the spacing between the members within a predetermined range. The intensity of the laser light diffused by the light diffusing member 103 greatly changes according to a distance from the light diffusing member 103, and attenuates as the distance from the light diffusing member 103 increases. As described above, since the light shielding member 301 is a member made of rubber or the like that shields light by absorbing light, if the light shielding member 301 is too close to the light diffusing member 103, there is a possibility that the light shielding member 301 melts down in a case where the intensity of the laser light emitted from the light diffusing member 103 is strong. In order to avoid such a situation from occurring, the spacing member 401 plays a role of adjusting the intensity of the laser light incident on the light shielding member 301 to a range that the light shielding member 301 can endure while preventing the insertion portion from being excessively thick by holding the interval between the light diffusing member 103 and the light shielding member 301 within a predetermined range. The spacing member 401 is inevitably irradiated with a laser beam stronger than the light shielding member 301. Therefore, unlike the light shielding member 301, the spacing member 401 is desirably made of a material that does not melt down even when irradiated with a relatively strong laser beam, and thus, for example, a metal or the like is desirable similarly to the protection member 102.

The spacing member 401 also plays a role of maintaining the overall shape of the insertion portion. Therefore, it is desirable that the spacing member 401 is made of a material having a certain degree of hardness, and in this respect, it is also desirable that the spacing member is metal. Since the insertion portion moves inside the subject while being deformed in accordance with the shape of the subject, the spacing member 401 that plays a decisive role in the overall shape of the insertion portion is required to have both a certain degree of hardness and flexibility. In order to satisfy such a demand with the spacing member 401 made of metal, it is desirable that the spacing member 401 includes a corrugated tube. Since the spacing member 401 includes the corrugated tube, the insertion portion can be configured to be neither too soft nor too hard, so that it is possible to realize a light guide unit that is easy to handle.

According to the light guide unit 400 configured as described above, since the risk that the light shielding member 301 is destroyed by the laser light can be further reduced, even if the optical fiber 101 is damaged, the light can be more reliably prevented from leaking from the light guide unit 400 to the outside. In addition, since moderate hardness and flexibility are both achieved by the spacing member 401, it is possible to obtain a light guide unit that is easy to handle. Note that the light guide unit 400 is similar to the light guide unit 200 and the light guide unit 300 in that the optical fiber 101 can be prevented from being damaged during normal use and manufacturing.

The above embodiments are specific examples for facilitating understanding of the invention, and embodiments of the present invention are not limited to these embodiments. The light guide unit and the endoscope system can be variously modified and changed without departing from the scope of the claims.

For example, in the above-described embodiment, it is assumed that the light guide unit is for a video scope including an imaging element, but the light guide unit may not include the imaging element. The light guide unit only needs to include a light guide member that guides laser light, and may be used only for illumination.

What is claimed is:

1. A light guide unit comprising:
   an optical fiber having an outer diameter;
   a protection tube surrounding the optical fiber,
   the protection tube including:
      a network structure comprising a metal material, and
      a gap formed in the network structure, the gap being smaller than the outer diameter and formed along an axial direction, and
   a light diffusing tube surrounding the protection tube and configured to diffuse narrow band light,
   wherein bumps are disposed on an exterior surface of the light diffusing tube.

2. The light guide unit according to claim 1, further comprising:
   a friction reducing tube configured to surround the protection tube.

3. The light guide unit according to claim 1, further comprising:
   a light shielding tube surrounding the light diffusing tube, the light diffusing tube configured to diffuse shielding light such that the light shielding tube is configured to surround the diffused shielding light.

4. The light guide unit according to claim 3, further comprising:
   a spacer disposed between the light diffusing tube and the light shielding tube within a predetermined range.

5. The light guide unit according to claim 4, wherein the spacer includes a corrugated tube.

6. The light guide unit according to claim 1, wherein the metal material has a higher absorption rate for narrow band light than for white light.

7. The light guide unit according to claim 1, wherein the gap is a rectangular gap, and the rectangular gap has a diagonal length smaller than the outer diameter of the optical fiber.

8. The light guide unit according to claim 1, wherein the light diffusing tube contains light diffusion particles.

9. The light guide unit according to claim 1, wherein the protection tube includes a plurality of gaps and each gap being spaced along the axial direction.

10. The light guide unit according to claim 1, wherein the optical fiber includes a plurality of bundled optical fibers.

11. The light guide unit according to claim 1, wherein
    the optical fiber is configured to guide narrow band light emitted from a laser light source, and
    the metal material has a higher absorptivity with respect to light belonging to a predetermined wavelength band among visible light bands than light belonging to a different band.

12. The light guide unit according to claim 1, wherein
    the optical fiber is configured to guide narrow band light belonging to a blue band emitted from a laser light source, and
    the metal material is stainless steel and has a higher absorptivity for light in a blue band than for light in a green band to a red band.

13. An endoscope system including the light guide unit according to claim 1, comprising:
    a laser light source configured to emit narrow band light guided by the optical fiber.

14. An endoscope system comprising:
    an endoscope,
    wherein the endoscope includes:
       the light guide unit according to claim 1, and
       a laser light source configured to emit narrow band light guided by the optical fiber.

15. The light guide unit according to claim 1, wherein the protection tube is configured to directly contact the optical fiber.

16. The light guide unit according to claim 2, wherein the friction reducing tube is integrally formed with the protection tube.

17. The light guide unit according to claim 1, wherein the metal material is a bent, flat linear member, and a cross-sectional shape of the metal material is a flat shape.

18. The light guide unit according to claim 1, wherein the bumps are translucent.

19. The light guide unit according to claim 2, further comprising:
    a light shielding tube surrounding the light diffusing tube, the light diffusing tube configured to diffuse shielding light such that the light shielding tube is configured to surround the diffused shielding light.

20. An endoscope system comprising:
    an endoscope,
    wherein the endoscope includes:
       the light guide unit according to claim 2, and
       a laser light source configured to emit narrow band light guided by the optical fiber.

* * * * *